United States Patent
Bohris

(10) Patent No.: US 11,607,236 B2
(45) Date of Patent: Mar. 21, 2023

(54) METHOD AND DEVICE FOR MONITORING A COUPLING QUALITY OF AN INTERFACE BETWEEN A LITHOTRIPER AND A PATIENT

(71) Applicant: Dornier MedTech Systems GmbH, Wessling (DE)

(72) Inventor: Christian Bohris, Wessling (DE)

(73) Assignee: Dornier MedTech Systems GmbH, Wessling (DE)

( * ) Notice: Subject to any disclaimer, the term of this patent is extended or adjusted under 35 U.S.C. 154(b) by 285 days.

(21) Appl. No.: 17/019,952

(22) Filed: Sep. 14, 2020

(65) Prior Publication Data

US 2021/0085351 A1 Mar. 25, 2021

(30) Foreign Application Priority Data

Sep. 20, 2019 (EP) .................................. 19198812

(51) Int. Cl.
*A61B 17/225* (2006.01)
*A61B 90/00* (2016.01)
(Continued)

(52) U.S. Cl.
CPC ........ *A61B 17/2258* (2013.01); *A61B 90/361* (2016.02); *G06T 5/40* (2013.01);
(Continued)

(58) Field of Classification Search
None
See application file for complete search history.

(56) References Cited

U.S. PATENT DOCUMENTS 5,269,306 A * 12/1993 Warnking ............ A61B 8/4281
600/443
6,508,774 B1 1/2003 Acker et al.
(Continued)

FOREIGN PATENT DOCUMENTS

DE 4125950 C1 11/1992
DE 102005039178 A1 3/2007

OTHER PUBLICATIONS

European Search Report for European Application No. 19198812.0, dated Nov. 25, 2019.

*Primary Examiner* — Xiaolan Xu
(74) *Attorney, Agent, or Firm* — Jason H. Vick; Sheridan Ross, PC

(57) ABSTRACT

The present invention provides for a method for continuously monitoring a coupling quality of a coupling interface between an acoustic energy source of a therapeutic device and a body surface area of a patient, comprising the steps of:
(f) obtaining a plurality of images of at least one predetermined first area of the coupling interface;
(g) extracting at least one first image characteristic of a predetermined first image of said plurality of images;
(h) extracting said at least one first image characteristic of at least one second image of said plurality of images, said at least one second image being temporally spaced apart from said predetermined first image;
(i) determining a quantitative parameter corresponding to a difference between said at least one first image characteristic of said predetermined first image and said at least one first image characteristic of said at least one second image, and
(j) actuating a signal if said quantitative parameter exceeds a predetermined reference threshold.

16 Claims, 6 Drawing Sheets

(51) Int. Cl.
  *G06T 7/136* (2017.01)
  *G06T 7/262* (2017.01)
  *G06T 7/32* (2017.01)
  *G06T 7/38* (2017.01)
  *G06T 7/13* (2017.01)
  *G06T 5/40* (2006.01)

(52) U.S. Cl.
  CPC ............... *G06T 7/13* (2017.01); *G06T 7/136* (2017.01); *G06T 7/262* (2017.01); *G06T 7/32* (2017.01); *G06T 7/38* (2017.01); *G06T 2207/30004* (2013.01)

(56) References Cited

U.S. PATENT DOCUMENTS

| | | | |
|---|---|---|---|
| 2013/0182957 A1* | 7/2013 | Wujcicki | G06V 20/588 |
| | | | 382/199 |
| 2019/0205515 A1* | 7/2019 | Lee | G06V 40/1318 |
| 2020/0193188 A1* | 6/2020 | Okada | G06V 10/25 |
| 2022/0277441 A1* | 9/2022 | Schlaudraff | G06V 10/431 |

* cited by examiner

METHOD AND DEVICE FOR MONITORING A COUPLING QUALITY OF AN INTERFACE BETWEEN A LITHOTRIPER AND A PATIENT

CROSS-REFERENCE TO RELATED APPLICATIONS

This application claims the benefit under 35 U.S.C. 119(a) to European Application No. 19198812.0, filed 20 Sep. 2019, the disclosure of which is incorporated herein by reference in its entirety.

SUMMARY

The present invention generally relates to the field of therapeutic devices utilising acoustic energy and in particular to the process of monitoring a coupling quality and detecting changes in the coupling quality between the therapy head of the therapeutic device and the patient's body. More specifically, the present invention relates to Extracorporeal Shock Wave Lithotripsy (ESWL) and an automatic method for monitoring the coupling quality of the acoustic coupling interface between the shock wave therapy head and the patient's body.

INTRODUCTION

In Extracorporeal Shock Wave Lithotripsy (ESWL), concrements, such as, for example, urinary stones or gallstones are disintegrated by focussed shock waves. Today, ESWL is a standard therapy in urolithiasis mainly competing with ureterorenoscopy and percutaneous nephrolithotomy as alternative procedures. Therapeutic devices utilising other acoustic energy sources, such as, for example, focussed or high-intensity ultrasound may be used to treat other medical disorders or for cosmetic purposes.

FIG. 1 shows a simplified schematic illustration of a typical lithotripter treatment head 15 comprising, inter alia, a shock wave source 12 including a shock wave focussing element (e.g. acoustic lens) 14, an imaging unit (for example an ultrasound imaging system, not shown) and a coupling device 16 between the shock wave source 12 and the patient's body 18.

During treatment between two- to three thousand shock waves are usually delivered at a frequency of 1 Hz to 2 Hz, thus, the total treatment duration is about 30 min to 40 min. The focussing element 14 (i.e. the acoustic lens) focusses the shock waves at a focal point 20, wherein the focal distance of the focal point 20 is fixed by the acoustic lens' geometry, typically between 140 mm and 180 mm from the acoustic lens 14. Prior to activating the shock wave source 12, the target 22 (e.g. urinary stone) within the patient's body 18 is aligned with the focal point 20 of the acoustic lens 14. Once activated, the shock waves are transmitted from the shock wave source 12 via a water-filled bellows or cushion (i.e. coupling device) 16 into the patient's body 18 to concentrate its energy onto target 22. The bellows or cushion 16 is pressed into contact with the patient's body 18 by simply increasing the pressure within the bellows or cushion 16. A coupling medium 24, such as a coupling gel, is applied to the contact surface of the bellows or cushion 16 "bridging" the interface between the bellows or cushion 16 and the skin surface of the patient's body 18 and therefore improving acoustic coupling for the shock waves.

Various studies have shown that even a few air bubbles 26 (or other disturbances in the coupling interface 27) within the coupling gel 24 can considerably reduce the efficacy of the shock waves. Due to its significant lower impedance, air fully blocks the shock waves and causes disturbances of the field, resulting in a significant loss of energy at the focal point. In practice, these air bubbles 26 may already be in the coupling gel 24 when provided by the manufacturer. More often, air bubbles may enter the coupling gel 24 when the coupling gel 24 is squeezed out of its container during application. Further, when arranging the bellows or cushion 16 into contact with the patient's body 18, air bubbles 26 may be trapped in the coupling interface 27 either at the initial setup at the beginning of the treatment, or in case the contact between the bellows or cushion 16 and the patient's body 18 is temporarily interrupted during the treatment. In addition to air bubbles 26 being trapped in the coupling gel 24, the coupling interface 27 may be disturbed if the contact pressure between the bellows or cushion 16 is too low and/or if there is only partial contact between the patient's body 18 and the bellows or cushion 16. Other potentially severe disturbances may arise, if the bellows or cushion 16 do not fit snugly against the patient's body 18 causing wrinkles or folds in the bellows or cushion contact surface. Further disturbances of the coupling interface 27 may be caused by any clothing or bed linen that gets trapped between the bellows or cushion 16 and the patient's body 18.

Once the therapy head 15 (i.e. including bellows or cushion 16) is arranged into contact with the patient's body 18, it is generally not possible to visually inspect the surface of the coupling interface 27. Thus, some commercially available lithotripters may comprise a surveillance camera 28 (i.e. a video camera) that is typically integrated within the shock wave source 12 allowing visualisation (i.e. imaging) of a region of interest (ROI) of the coupling interface 27 that is displayed on a monitor 30 (e.g. Dornier OptiCouple®). A light source 29 (e.g. spot light) may be provided to illuminate the coupling interface 27. The light source 29 may be any suitable light source (e.g. white LED) and may be positioned separate from the camera 28 so as to provide a desired illumination characteristic. Through the surveillance camera 28, an operator can monitor the coupling interface 27 and detect disturbances, such as, for example, trapped air bubbles 26, an incomplete coupling or folds/wrinkles of the bellows or cushion 16 contact surface etc. and the operator may remove any of these disturbances by simply wiping over the contact surface of the bellows or cushion 16.

Alternatively, an inline ultrasound scanner, i.e. a diagnostic ultrasound transducer integrated into the shock wave source 12, may be used to monitor the coupling interface 27. However, inline ultrasound scanner only allow detection in the actual scanning plane, so that a 180° rotation of the ultrasound transducer is required for a complete scan of the entire area of the coupling interface 27, wherein a video camera 28 allows immediate and real-time inspection of the entire area of the coupling interface 27.

In use, the coupling quality of the coupling interface 27 should be checked especially after the initial treatment setup is complete, i.e. the patient is suitably positioned relative to the therapy head 15 and the bellows or cushion 16 is brought into contact with the patient's body 18. Often, the coupling quality of the coupling interface 27 remains unaffected during the actual treatment, however, the coupling quality of the coupling interface 27 may be disturbed by inadvertent patient movement, or by repositioning of the patient in order to adjust the shock wave target position, or by changing the coupling settings for whatever reason.

Consequently, it is crucial that the operator regularly inspects the coupling interface 27 throughout the entire duration of the treatment. Though, since a typical treatment can last between 30 min and 40 min, regular inspection of the coupling interface 27 can be a rather fatiguing task, especially as disturbance may only occur infrequently.

Currently available monitoring systems are based on image processing to evaluate the size of the coupling area blocked by air inclusions in the coupling gel by differentiating between areas that represent air from areas that represent no air, such that, if the size of the air inclusions is above a certain threshold, the operator may be alarmed. However, this approach comes with considerable practical problems. For example, the differentiation between pixels that represent air and pixels that represent the gel is non-trivial and depends very much on the present image contrast, illumination of the coupling interface, the camera settings, the colour of the applied coupling gel and even the patient's skin colour. Also, hairs, pigmental moles or tattoos are likely to affect the evaluation. Also, the bellows or cushion of the coupling device 16 are used to adapt for different penetration depths, i.e. changing the distance between camera 28 and the coupling interface 27, so that the images size of the air inclusion appears different with varying distance between the camera 28 and the coupling interface 27, making it difficult to determine an absolute value of the air inclusion. Further, the amount of the entrapped air is only of limited use when describing the impact on the transmission, i.e. air bubbles near the shock wave centre axis is known to affect the transmission more than air bubbles that are further away from the central axis, because the transmittal shock wave energy flux density is at its maximum at the centre axis. Also, numerous small air bubbles may affect the transmission more than a single air bubble of the same size, because the scattering surface of a bubble is larger than the bubble itself.

Therefore, it is an object of the present invention to provide an improved method and device for monitoring a coupling quality of the coupling interface 27 between a lithotripter and a patient. In particular, it is an object of the present invention to provide automatic image-based surveillance of a coupling quality of the coupling interface 27 with improved reliability and ease of use for the operator.

According to a first aspect of the invention, there is provided a method for continuously monitoring a coupling quality of a coupling interface between an acoustic energy source of a therapeutic device and a body surface area of a patient, comprising the steps of:
(a) obtaining a plurality of images of at least one predetermined first area of the coupling interface;
(b) extracting at least one first image characteristic of a predetermined first image of said plurality of images;
(c) extracting said at least one first image characteristic of at least one second image of said plurality of images, said at least one second image being temporally spaced apart from said predetermined first image;
(d) determining a quantitative parameter corresponding to a difference between said at least one first image characteristic of said predetermined first image and said at least one first image characteristic of said at least one second image, and
(e) actuating a signal if said quantitative parameter exceeds a predetermined reference threshold.

Preferably, the method may further comprise the step of:
(f) repeating steps (c) to (e) for at least one other image of said plurality of images that is temporally spaced apart from said predetermined first image and said at least one second image.

This provides the advantage of an automated objective and reliable method for continuously and unambiguously monitoring changes in the quality of a coupling interface between the therapy head 15 and the patient. In particular, the present invention provides the advantage of detecting any changes in a predetermined image parameter that represents a coupling quality throughout the entire treatment duration, irrespective of any variations in the system settings or treatment setup for individual patients. That is, the detected change is somewhat normalised for the conditions existing at the time of treatment, therefore, making the automatic method more accurate and reliable over existing monitoring techniques.

Advantageously, said at least one first image characteristic may be any one of a tonal image distribution, a frequency spectrum and an image feature characteristic. In one embodiment, said tonal image distribution may be a histogram of a probability distribution function of image brightness of any one of said plurality of images. Preferably, said frequency spectrum may be a 2D Fourier spectrum of any one of said plurality of images.

In another embodiment, said image feature characteristic may be a length of one or more edge features detected by an edge detection algorithm within any one of said plurality of images. Advantageously, said length may be a total length of said one or more edge features. Even more advantageously, said edge detection algorithm may utilise a Sobel operator.

Advantageously, said quantitative parameter may be based on a cross-correlation between said at least one first image characteristic of said predetermined first image and said at least one first image characteristic of said at least one second image.

In one embodiment, said quantitative parameter may be a difference in length between the length of said one or more edge features detected in said first image and the length of said one or more edge features detected in any one of said at least one second image.

Advantageously, said predetermined reference threshold may be a maximum deviation from said at least one first image characteristic of said predetermined first image.

Advantageously, said at least one second image and said at least one other image of said plurality of images may be a sequence of images subsequent to said predetermined first image and spaced apart at a predetermined time interval.

Advantageously, said signal may be a visual and/or audible signal.

Advantageously, said predetermined area may be adaptable during use. This provides the advantage that the ROI can change (e.g. size) or "move" its position so as to optimise the predetermined area (in case f patient movement etc.). The adaptable ROI may be provided by an algorithm within the image processor, wherein relevant parameters for the optimisation of the ROI may be set by the operator.

According to another aspect of the present invention, there is provided a device for continuously monitoring a coupling quality of a coupling interface between an acoustic energy source of a therapeutic device and a body surface area of a patient, comprising:
an imaging system, configured to capture and display a plurality of images of at least one predetermined first area of the coupling interface, and
an image processor, adapted to execute the method according to the first aspect of the invention.

Advantageously, said imaging system may comprise any one of an optical camera and a sonograph.

According to yet another aspect of the present invention, there is provided a computer readable storage medium having embodied thereon a computer program, when executed by a computer processor that is configured to perform the method according to the first aspect of the present invention.

BRIEF DESCRIPTION OF THE DRAWINGS

Example embodiments of the description will now be described, by way of example only, with reference to the accompanying drawings, in which.

DETAILED DESCRIPTION OF THE PREFERRED EMBODIMENT(S)

The described example embodiment relates to an Extracorporeal Shock Wave Lithotripter (ESWL) and, in particular, to monitoring/surveillance of a coupling interface between the therapy head of the Lithotripter and the patient's body in order to detect changes of the coupling quality to then notify the operator in case the change exceeds a predetermined threshold. It is understood by the person skilled in the art that the present invention is not limited to shock wave lithotripters as described in the specific example but is equally applicable to other therapeutic devices using any other suitable acoustic energy source (e.g. shock waves, ultrasound).

Certain terminology is used in the following description for convenience only and is not limiting. In particular, it should be appreciated that the terms 'determine', 'calculate' and 'compute' and variations thereof may be used interchangeably and include any type of methodology, process, mathematical operation or technique. The terms 'generating' and 'adapting' may also be used interchangeably describing any type of computer image processing. In addition, the term 'pixel' is understood to mean a digital picture element, or the smallest unit of a display memory that can be controlled.

Further, unless otherwise specified (e.g. by providing a temporal order), the use of ordinal adjectives, such as, "first", "second", "third" etc. merely indicate that different instances of like objects are being referred to and are not intended to imply that the objects so described must be in a given sequence, either temporally, spatially, in ranking or in any other manner.

Figure 1:
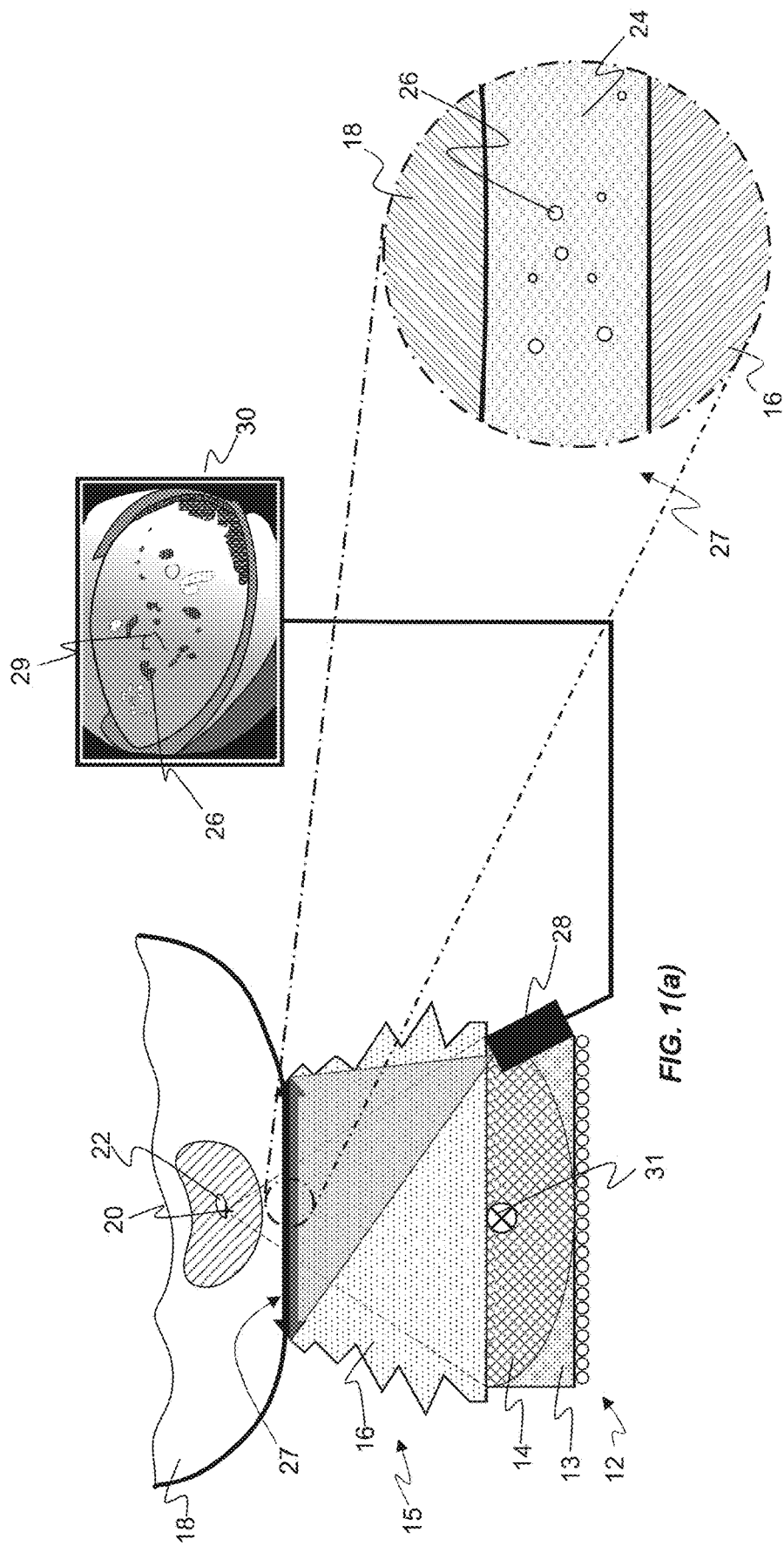
FIGS. 1(a) and 1(b) (Prior Art) show a schematic illustration (cross section) of the therapy head and video monitor of a ESWL in use with a patient, the therapy head including bellows, acoustic lens and shock wave source, as well as, the OptiCouple® feature (video imaging system)
Figure 2:
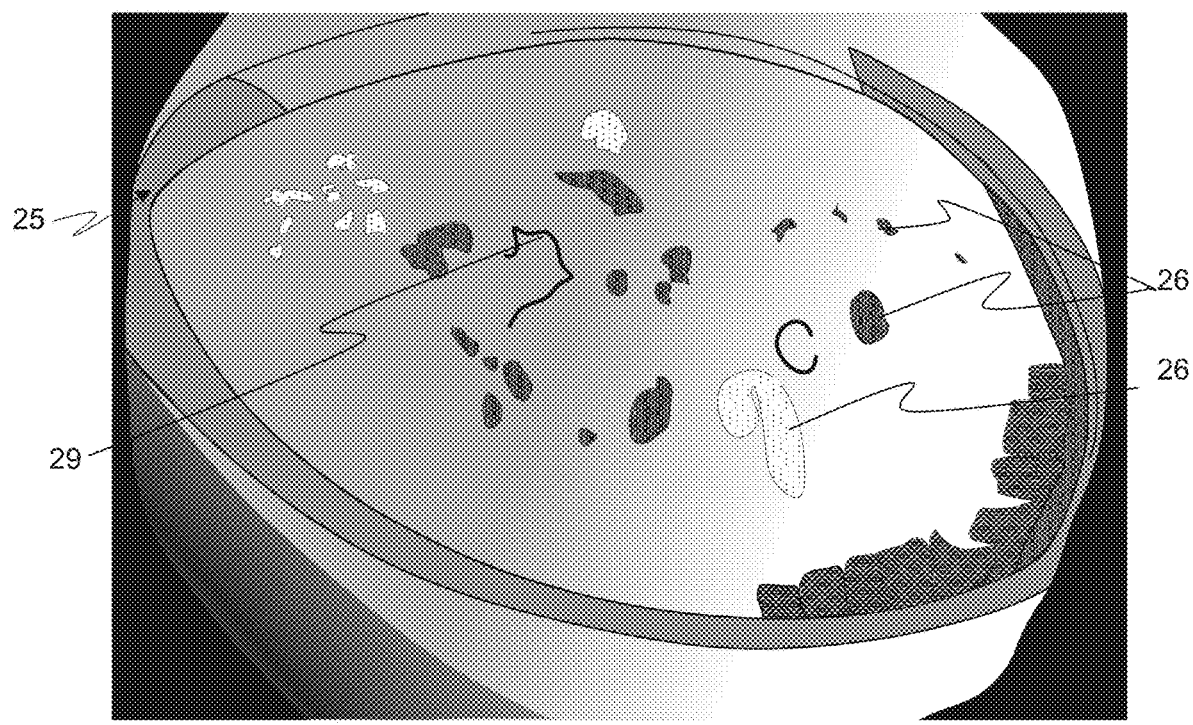
FIGS. 2(a) and 2(b) show a simplified schematic illustration of an image of the coupling interface (coupling gel layer at region of interest), (a) showing air bubbles (bright or dark due to different lighting conditions), as well as, hairs, and (b) without any trapped air bubbles.
Figure 2:
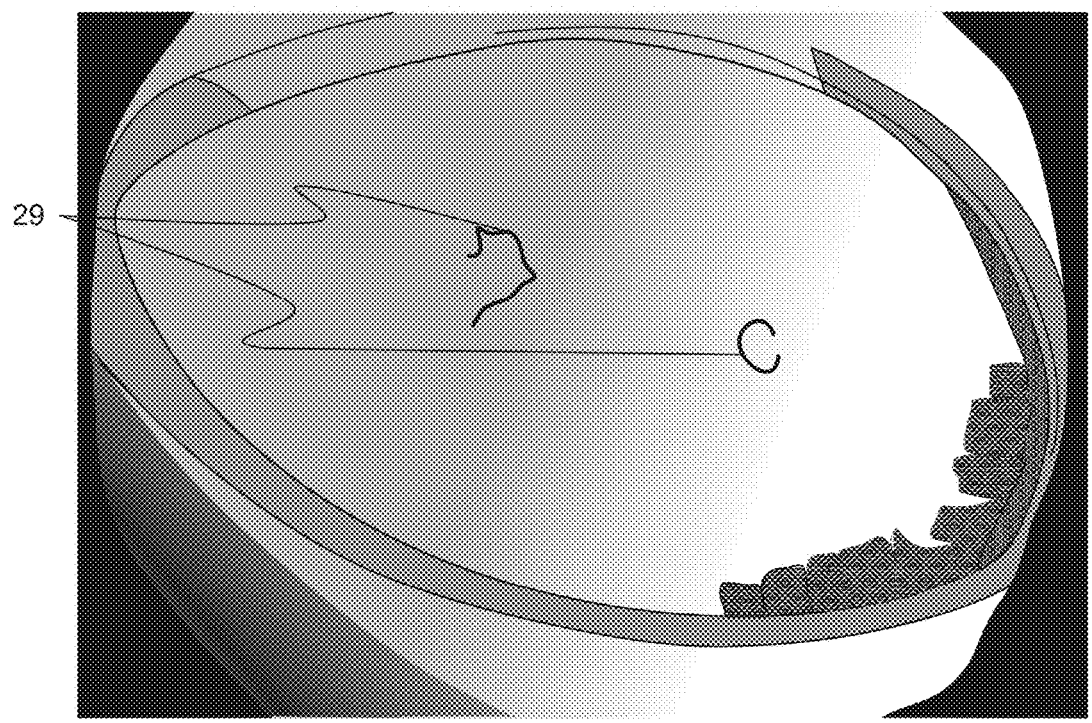
Figure 3:
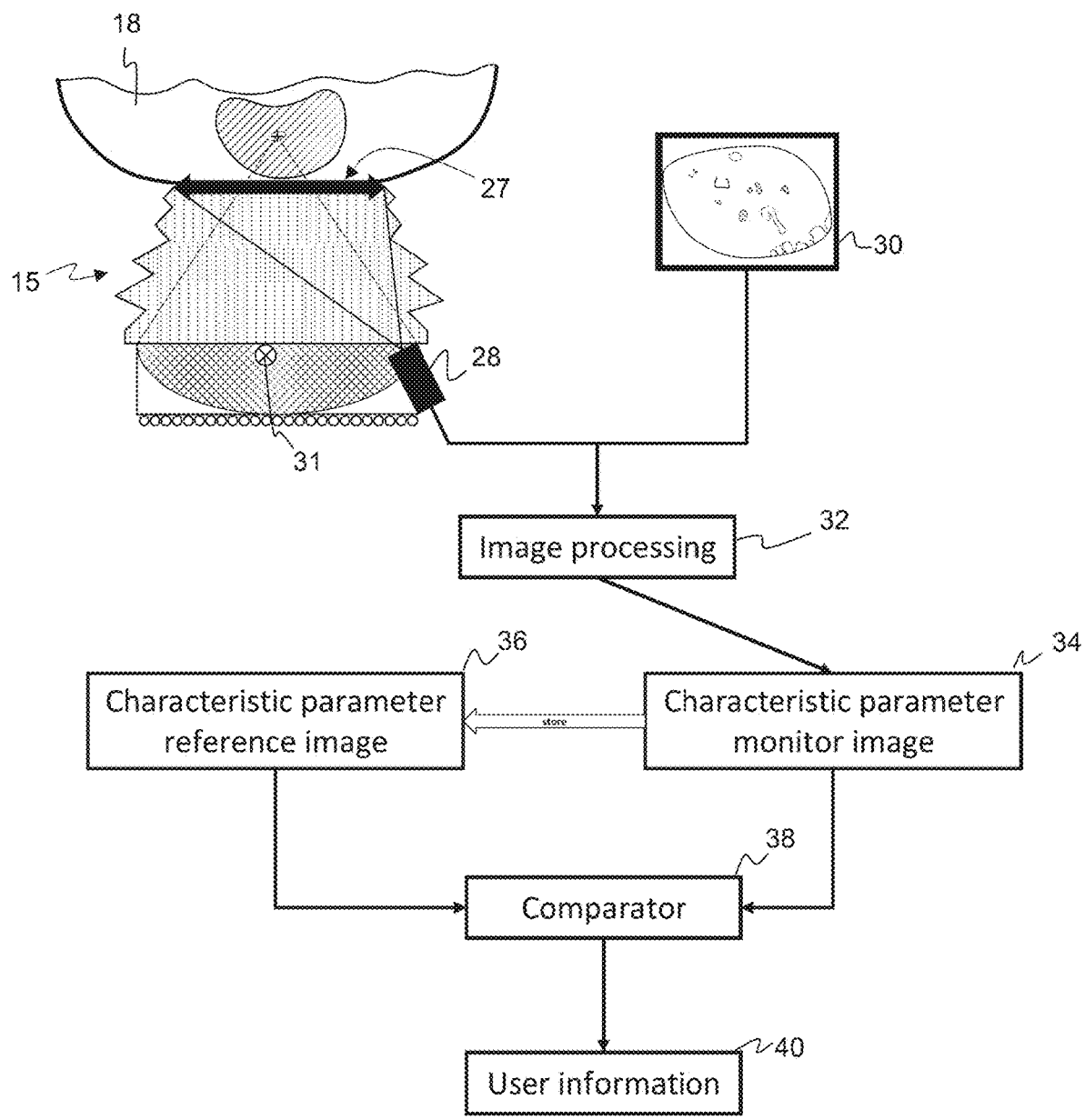
FIG. 3 shows a simplified schematic and flowchart of the device and method of the present invention.

Referring now to FIGS. 1 to 3, a portion of a commercial Lithotripter system is illustrated schematically (i.e. the therapy head). The arrangement is suited for detecting the quality of the coupling interface 27 and provide the method of the present invention. In particular, FIG. 1 (a) shows a cross section of the therapy head 15 when operably coupled to the patient's body 18. The therapy head 15 comprises a shock wave source 12 including an acoustic lens 14 (usually immersed in a water bath 13) and a coupling device, such as, for example a cushion or bellows 16 (typically filled with water 13). A coupling gel 24 is evenly applied to a contact surface of the bellows 16 forming a coupling interface 27 with the patient's body 18. The rim 25 indicates the boundary of the contact surface with the bellows 16. A video camera 28 is positioned so as to acquire images (e.g. digital images) of a region of interest of the coupling interface 27. Typically, the video camera 28 is integrated into the shock wave source 12 so as to allow continuous monitoring of the coupling interface 27. A monitor 30 is provided to display real-time images (snap-shot or video) for visual inspection. A light source 31 (e.g. white LED) is provided at the rim of the lens 14. In this particular example, the light source 31 may be radially spaced apart from the camera 28 (e.g. 90°) so as to provide a relative inhomogeneous illumination in order to display occurring air bubbles either relatively bright or dark. Such inhomogeneous illumination can be advantageous when identifying or detecting air bubbles within the method of the present invention.

During treatment setup, the therapy head 15 is positioned so that the target area 22 is within the focal point 20 of the acoustic lens 14. The bellows 16 (with applied coupling gel 24) is then inflated to move into contact with the patient's body 18 forming a coupling interface 27, preferably without trapped air bubbles 26 or other disturbances. The operator visually inspects the image of the coupling interface 27 for any detrimental disturbances (e.g. air bubbles 24, hairs 29, folds or wrinkles etc.) and may wipe over the contact surface of the bellows 16 so as to remove such trapped air bubbles 26 and/or folds.

A region of interest (ROI) may be determined by the operator (e.g. user defined) or by an image processing algorithm (depending on image parameters set by the operator). The determined ROI may either be static during operation (e.g. a set window size) but may also be adapted during operation (e.g. an image processing function may adjust the ROI size and/or position during operation in accordance with pre-set parameters of the interface 27).

Once the coupling quality is acceptable, shock wave treatment commences, typically for a duration of 30 min to 40 min during which inadvertent patient movement may cause a change in the coupling quality of the coupling interface 27, for example, air gets trapped again in the coupling gel 24, body hair 29 may be arranged so as to provide a disturbance, or folds or wrinkles in the bellows 16 contact surface may be effected by the movement.

As can be understood by a person skilled in the art, it would be difficult to either determine from a single image, whether or not, the coupling quality if sufficient for the whole duration of the treatment. Also, there may only be partial coupling caused by insufficient coupling pressure (i.e. the pressure within the bellows 16) or disturbances attributable to a particular treatment situation (e.g. when treating a small child). Pigmental moles or hairs may be difficult to distinguish from trapped air bubbles 26 at different lighting.

Depending on the present lighting, the brightness of trapped air bubbles 26 may vary between individual air bubbles (i.e. some air bubbles appear brighter and others appear darker relative to the background) and compared to the coupling gel 24.

As illustrated in FIG. 3, the present invention provides a method for automatically and unambiguously monitor the coupling interface 27 and detect any changes to the quality of the coupling interface 27, as well as, visually and/or audibly indicate when the detected change exceeds a predetermined threshold, irrespective of the nature of the disturbances, the current setup or treatment situation.

During operation (i.e. when the initial coupling quality is acceptable and shock wave therapy has commenced), at least one first reference image is obtained (i.e. stored in a suitable storage medium) from the coupling interface 27 and subjected to image processing 32 to extract at least one image characteristic 34, such as, for example, one or more characteristic parameter(s) and/or one or more characteristic function(s). The reference image 36 may be selected at a predetermined time (preferably the first image) and/or having a predetermined minimum coupling quality based on the chosen image characteristic. The image characteristic utilised may be any one of a distribution function (histogram) of brightness, a total edge length detected in the image, or a spatial Fourier spectrum.

During the duration of the treatment, subsequent images are continuously obtained from the coupling interface 27 at a predetermined time interval and each one is subjected to image processing 32 so as to extract the at least one image characteristic (e.g. total edge length, brightness histogram or Fourier spectrum etc). The extracted image characteristic 34 is then compared to the image characteristic of the predetermined reference image 36 using a comparator. Further, the comparator 38 comprises specific values for a maximum deviation from any one of the selectable image characteristics, any one of which may be utilised to determine a significant change from the reference image. Thus, in case the image characteristic of any one of the subsequent images exceeds the maximum deviation from the image characteristic of the reference image, a signal is triggered to notify the operator 40. The signal may be any one of an audible or visual alarm.

The time interval between subsequent images may simply be the frequency of the video camera 28, or a specific time interval may be set by the operator, for example, the time interval of obtained subsequent images may be in line with the frequency of the shock waves, or any other interval suitable to continuously monitor the coupling interface 27 and detect significant changes of a coupling quality.

Further, it is understood by the person skilled in the art, that the operator may select any one of the available image characteristics prior to the start of the treatment, to be used for detecting changes in the coupling quality of the coupling interface 27. Also, the maximum deviation for each of the available image characteristics may be individually set by the operator and/or may be pre-set in the comparator during manufacture.

Figure 4:
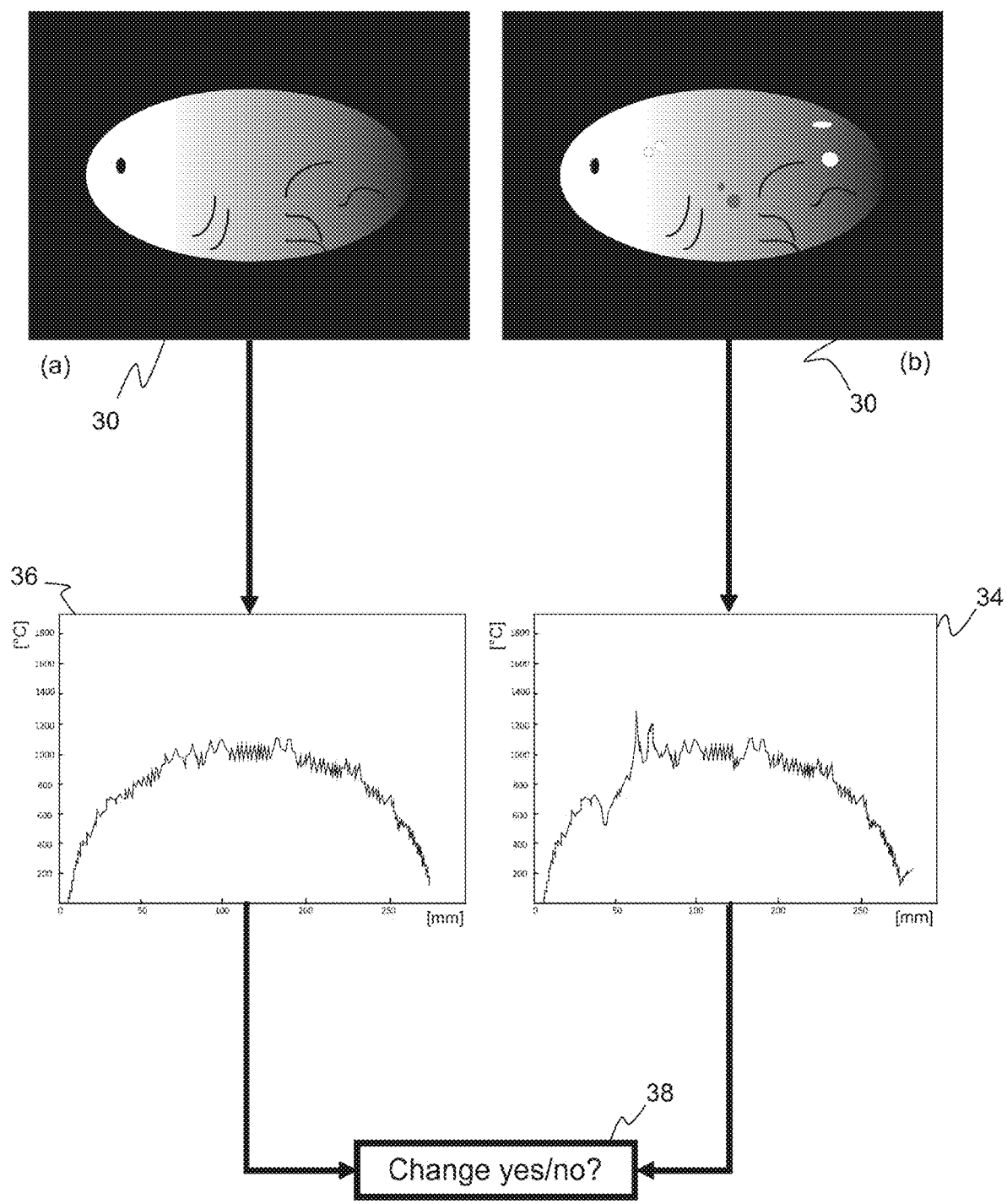
FIG. 4 shows a simplified illustration of the predetermined reference image and a presently monitored image of the coupling interface, as well as, respective diagrams of the determined characteristic parameter, in this case, the distribution function (histogram) of the image brightness.

FIG. 4 illustrates the method of the present invention when using (e.g. pre-selecting) a distribution function (histogram) of brightness. FIG. 4 (*a*) represents the reference image and FIG. 4(*b*) represents one of the subsequently obtained images. The reference numerals used are in line with the method illustrated in FIG. 3, i.e. image displayed on the monitor 30, extracted image characteristic of reference image 36 and a subsequent image 34, and action of comparator 38. The image shows an elliptical coupling interface illuminated by a spot light on its left side. A small air bubble is shown on the left side of the reference image, which may be acceptable to the operator, as it is not at the centre axis of the shock waves. The reference image also includes hairs 29. As discussed earlier, an image processing unit of the system calculates a histogram of the brightness. The x-axis of the histogram represents image brightness (0=black, 255=white), and the y-axis of the histogram represents the number of pixels. The black background is suppressed by setting the number of black pixels to zero. Though, a relevant region of interest may be defined by the operator. As is understood by the person skilled in the art, the method of the present invention does not require the reference image to be without any disturbances at all. The subsequent image obtained shows additional disturbances, e.g. trapped air bubbles 26. The extracted histogram differs from the histogram for the reference image. In particular, the rather smooth brightness distribution of the reference image shows additional maxima and minima in the histogram of the subsequently obtained image. The differences are identified by the comparator, for example, by using known cross correlation techniques.

Figure 5:
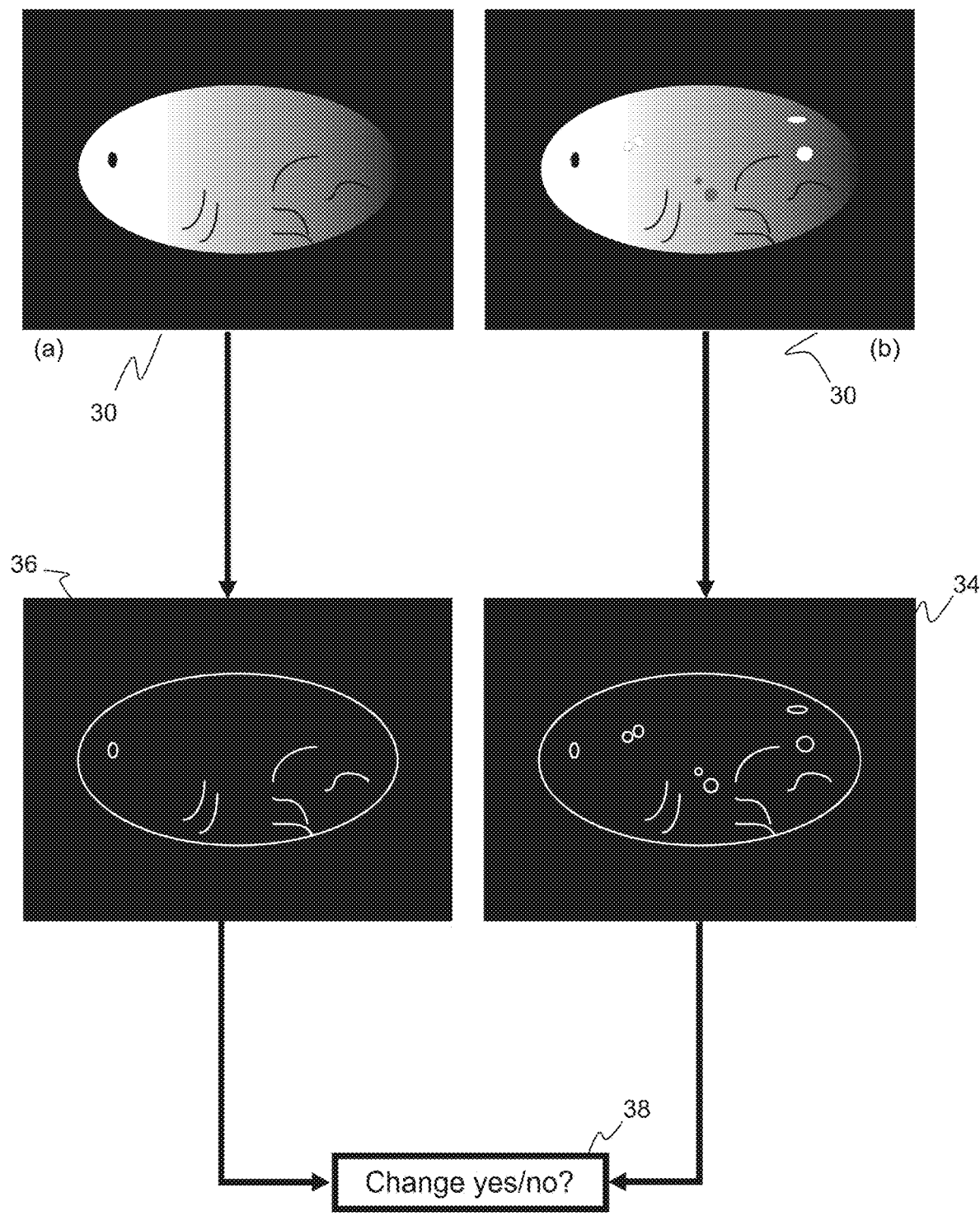
FIG. 5 shows a simplified illustration of the predetermined reference image and a presently monitored image of the coupling interface, as well as, respective processed images after edge detection, the total edge length being the characteristic parameter.

FIG. 5 illustrates the method when using total edge length as the image characteristic. In particular, the image processing unit applies an edge detection filter to enhance those image pixels which represent edges within the image, e.g. air bubbles or hairs show edges. The edge detection is independent of brightness changes of the background (i.e. coupling gel). Again, the method of the present invention does not require the reference image to be without any disturbances (i.e. edges at all). In this particular example, a horizontal and vertical Sobel kernel was convoluted with the image data. FIG. 5(*a*) represents the reference image and FIG. 5(*b*) represents one of the subsequently obtained images. The additional edges found in the subsequent image present additional disturbances (e.g. air bubbles 26) which are identified by the comparator, e.g. by counting the number of pixels representing edge (i.e. pixels with a brightness above a set threshold). If the total number of pixels or total length of edges exceeds a predetermined maximum deviation from the edges of the reference image, a visual and/or audible signal is trigged to notify the operator.

Figure 6:
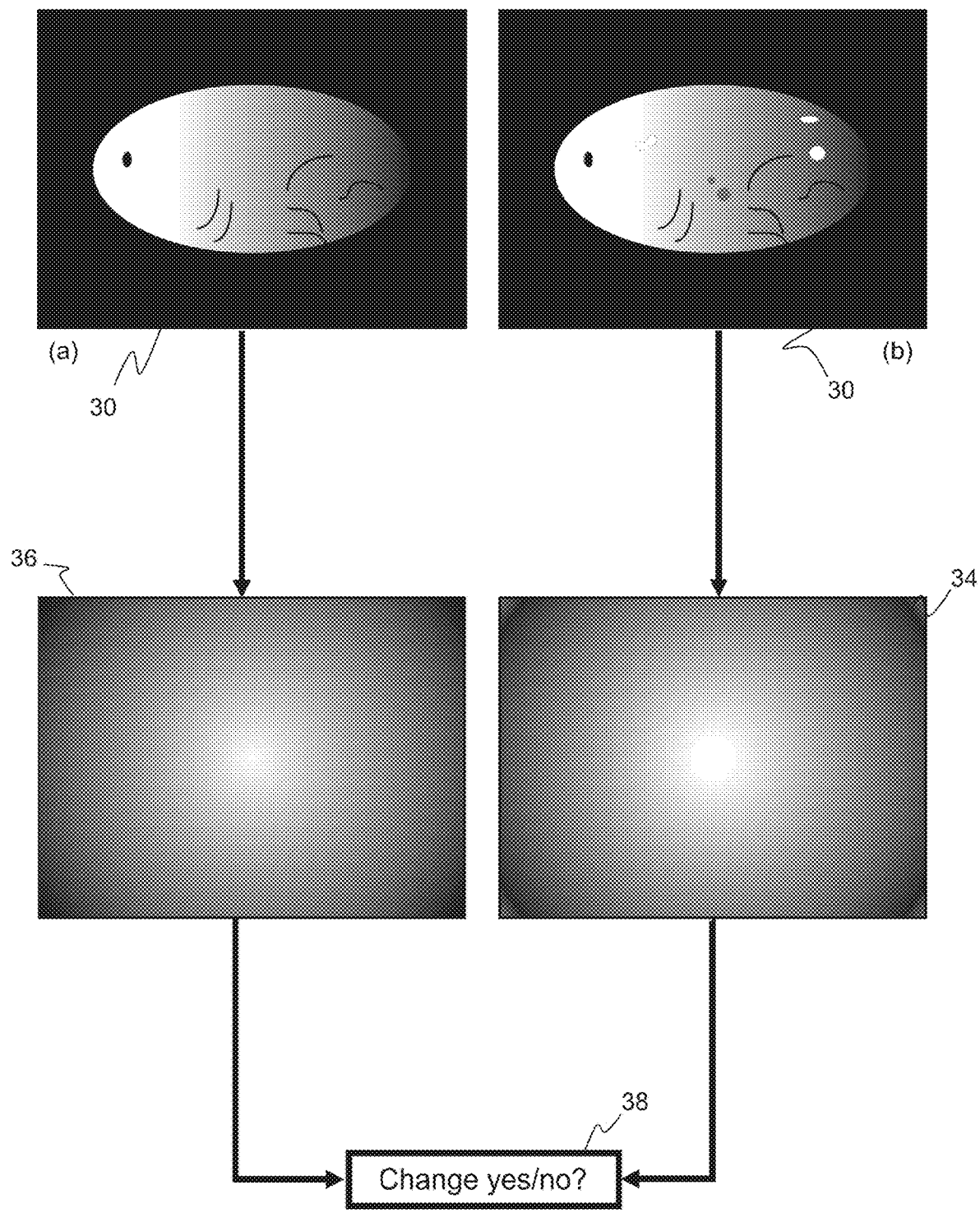
FIG. 6 shows a simplified illustration of the predetermined reference image and a presently monitored image of the coupling interface, as well as, respective visualisation of the spatial Fourier spectrum after applying a 2D Fourier transform to each one of the images.

FIG. 6 illustrates the method when using a spatial Fourier spectrum as the image characteristic. Here, the image processor applies, for example, a 2-dimensional Fourier transform (FFT) to the image data. The Fourier transform contains all image information, wherein image variations are translated into spatial frequencies. In this particular example, the low frequencies are at the image centre of the FFT representation. FIG. 6(*a*) represents the reference image and FIG. 6(*b*) represents one of the subsequent images. The additional disturbances shown in the subsequent image induce changes in the frequency distribution of the FFT. The changes in the FFT can b identified by the comparator, in particular, by using a range of Fourier coefficients that are most sensitive to additional disturbances.

It will be appreciated by persons skilled in the art that the above embodiment(s) have been described by way of example only and not in any limitative sense, and that various alterations and modifications are possible without departing from the scope of the invention as defined by the appended claims. In particular, it is understood by the skilled person in the art, that any other suitable image characteristic may be used to monitor and detect changes of a coupling quality of a coupling interface (image). Further, the invention is not limited to shock wave therapy only but is equally suitable for any other therapy device using an acoustic energy source, including extracorporeal shock waves (ESWs), pressure waves (PWs), as well as, ultrasound (US).

The invention claimed is:

1. A method to continuously monitor a coupling quality of a coupling interface between an acoustic energy source of a therapeutic device and a body surface area of a patient, comprising:
   (a) obtaining a plurality of images of at least one predetermined first area of the coupling interface;
   (b) extracting at least one first image characteristic of a predetermined first image of said plurality of images;
   (c) extracting said at least one first image characteristic of at least one second image of said plurality of images, said at least one second image being temporally spaced apart from said predetermined first image;
   (d) determining a quantitative parameter corresponding to a difference between said at least one first image characteristic of said predetermined first image and said at least one first image characteristic of said at least one second image, and
   (e) actuating a signal if said quantitative parameter exceeds a predetermined reference threshold, wherein said predetermined reference threshold is a maximum deviation from said at least one first image characteristic of said predetermined first image.

2. The method according to claim 1, further comprising the step of:
   (f) repeating steps (c) to (e) for at least one other image of said plurality of images that is temporally spaced apart from said predetermined first image and said at least one second image.

3. The method according to claim 1, wherein said at least one first image characteristic is any one of a tonal image distribution, a frequency spectrum and an image feature characteristic.

4. The method according to claim 3, wherein said tonal image distribution is a histogram of a probability distribution function of image brightness of any one of said plurality of images.

5. The method according to claim 3, wherein said frequency spectrum is a 2D Fourier spectrum of any one of said plurality of images.

6. The method according to claim 3, wherein said image feature characteristic is a length of one or more edge features detected by an edge detection algorithm within any one of said plurality of images.

7. The method according to claim 6, wherein said length is a total length of said one or more edge features.

8. The method according to claim 6, wherein said edge detection algorithm utilises a Sobel operator.

9. The method according to claim 1, wherein said quantitative parameter is based on a cross-correlation between said at least one first image characteristic of said predetermined first image and said at least one first image characteristic of said at least one second image.

10. The method according to claim 6, wherein said quantitative parameter is a difference in length between the length of said one or more edge features detected in said first image and the length of said one or more edge features detected in any one of said at least one second image.

11. The method according to claim 1, wherein said at least one second image and said at least one other image of said plurality of images are a sequence of images subsequent to said predetermined first image and spaced apart at a predetermined time interval.

12. The method according to claim 1, wherein said signal is a visual and/or audible signal.

13. The method according to claim 1, wherein said predetermined area is adaptable during use.

14. A device to continuously monitor a coupling quality of a coupling interface between an acoustic energy source of a therapeutic device and a body surface area of a patient, comprising:
   an imaging system, configured to capture and display a plurality of images of at least one predetermined first area of the coupling interface;
   an image processor configured to:
   (f) obtain a plurality of images of at least one predetermined first area of the coupling interface;
   (g) extract at least one first image characteristic of a predetermined first image of said plurality of images;
   (h) extract said at least one first image characteristic of at least one second image of said plurality of images, said at least one second image being temporally spaced apart from said predetermined first image;
   (i) determine a quantitative parameter corresponding to a difference between said at least one first image characteristic of said predetermined first image and said at least one first image characteristic of said at least one second image, and
   (j) actuate a signal if said quantitative parameter exceeds a predetermined reference threshold, wherein said predetermined reference threshold is a maximum deviation from said at least one first image characteristic of said predetermined first image.

15. The device according to claim 14, wherein said imaging system comprises any one of an optical camera and a sonograph.

16. A non-transitory computer readable information storage medium having stored thereon instructions, that when executed by a computer processor perform a method comprising:
   obtaining a plurality of images of at least one predetermined first area of the coupling interface;
   extracting at least one first image characteristic of a predetermined first image of said plurality of images;
   extracting said at least one first image characteristic of at least one second image of said plurality of images, said at least one second image being temporally spaced apart from said predetermined first image;
   determining a quantitative parameter corresponding to a difference between said at least one first image characteristic of said predetermined first image and said at least one first image characteristic of said at least one second image, and
   actuating a signal if said quantitative parameter exceeds a predetermined reference threshold, wherein said predetermined reference threshold is a maximum deviation from said at least one first image characteristic of said predetermined first image.

* * * * *